United States Patent [19]

Nguyen et al.

[11] Patent Number: 5,043,330

[45] Date of Patent: Aug. 27, 1991

[54] PHENOL SUBSTITUTED GEM-DIPHOSPHONATE DERIVATIVES, PROCESS FOR THEIR PREPARATION AND PHARMACEUTICAL COMPOSITIONS CONTAINING THEM

[75] Inventors: Lân Nguyen; Eric Niesor, both of Nyon; Hieu Phan, Tannay; Pierre Maechler, Plan-les-Ouates; Craig Bentzen, Bogis-Bossey, all of Switzerland

[73] Assignee: Symphar S.A., Le Lignon, Switzerland

[21] Appl. No.: 323,334

[22] Filed: Mar. 14, 1989

[30] Foreign Application Priority Data

Mar. 31, 1988 [CH] Switzerland ............... 1239/88

[51] Int. Cl.$^5$ ............... C07F 9/58; C07F 9/40; A61K 31/675
[52] U.S. Cl. ............... 514/107; 558/161; 558/77; 558/83; 562/19; 562/21
[58] Field of Search ............... 562/21, 19; 558/162, 558/77, 83, 161, 73; 514/107

[56] References Cited

U.S. PATENT DOCUMENTS

| | | | |
|---|---|---|---|
| 3,299,123 | 1/1967 | Fitch et al. | 558/162 |
| 3,404,178 | 10/1968 | Roy | 562/21 |
| 4,309,364 | 1/1982 | Bentzen et al. | 562/21 |
| 4,696,920 | 9/1987 | Bentzon et al. | 514/89 |

FOREIGN PATENT DOCUMENTS

| | | |
|---|---|---|
| 15370 | 9/1980 | European Pat. Off. . |
| 1173041 | 3/1986 | European Pat. Off. . |
| 100718 | 10/1987 | European Pat. Off. . |
| 2043072 | 10/1980 | United Kingdom . |

OTHER PUBLICATIONS

Gross et al., J. fur frakt. Chemie. Band 317, (6), 1975, pp. 890-896.

Gross, et al., J. fur prakt. Chemie, Band 320, (2), 1978, pp. 344-350.

Insull et al., JAMA, Jan. 29, 1984, 251(3), p. 351-364.
Insulh et al., JAMA, 1984: 251, 365-374.
Rack, et al., New Eng. J. Med., 317(20), 1987.
Lehnapt, Tetrahedron 30, pp. 301-305, 1984.
"Entalkylierung von Phosphonsaureestern mit labilen funktionellen Gruppen mittels Trimethylsilylbromid", Journal f. prakt. Chemie., vol. 320, No. 2, 1978. by H. Gross et al., pp. 344-350.
"Reduction in Incidence of Coronary Heart Disease", Journal of The American Medical Association, vol. 251, No. 3, Jan. 1984, pp. 351-364.
"The Relationship of Reduction in Incidence of Coronary Heart Disease to Cholesterol Lowering", Journal of the American Medical Association, vol. 251, No. 3, Jan. 1984, pp. 365-374.
"Helsinki Heart Study: Primary-Prevention trial with Gemfibrozil in Middle-Aged Men with Dysliphidemia", The New England Journal of Medicine, vol. 317, No. 20, Nov. 12, 1987, by M. Frick et al., pp. 1237-1245.

Primary Examiner—Mukund J. Shah
Assistant Examiner—E. C. Ward
Attorney, Agent, or Firm—Young & Thompson

[57] ABSTRACT

The invention relates to new gem-diphosphonates derivatives substituted by phenol groups of formula (I):

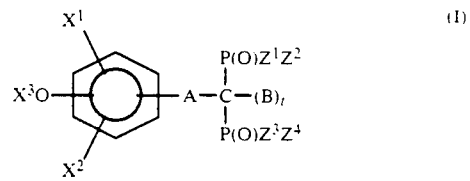

as well as the process for their preparation and the pharmaceutical compositions containing them.

16 Claims, No Drawings

PHENOL SUBSTITUTED GEM-DIPHOSPHONATE DERIVATIVES, PROCESS FOR THEIR PREPARATION AND PHARMACEUTICAL COMPOSITIONS CONTAINING THEM

This invention relates to a novel class of compounds, phenol substituted gem-diphosphonate derivatives as well as the process for preparing such compounds. It further relates to pharmaceutical compositions containing the above-mentioned compounds especially for the treatment of hyperlipidemia.

Many epidemiologic studies have shown that people with high levels of serum cholesterol are at high risk of developing coronary artery diseases. The convincing and definitive evidence that lowering serum cholesterol with the aid of hypocholesterolemic drugs reduces the risk of coronary heart diseases was provided by the Lipid Research Clinics Coronary Primary Prevention Trial reports (The Lipid Research Clinics Coronary Primary Prevention Trial results. I. Reduction in incidence of coronary heart disease. Journal of the American Medical Association 251, p. 351-364, 1984. The Lipid Research Clinics Coronary Primary Prevention Trial results. II. The relationship of reduction in incidence of coronary heart disease to cholesterol lowering. Journal of the American Medical Association 251, p. 365-374, 1984).

In addition, the most recent report from the Helsinki study showed that gemfibrozil treatment, which was associated with the modification of the serum lipoprotein levels and decreased plasma triglycerides, reduces the incidence of coronary heart disease in men with dyslipemia (The New England Journal of Medicine 317 (20), p. 1237-1245, 1987).

The phenol substituted gem-diphosphonates were tested and discovered to be potent hypolipidemic and lipid altering agents, in addition some were found to possess hypotensive activity. These gem-diphosphonates are therefore potentially useful agents for the treatment of dyslipemias and associated cardiovascular diseases.

H. Gross and coworkers have described the synthesis of (3,5-ditertiarybutyl-4-hydroxyphenyl)methylidene diphosphonic acid and its Me, Et and Pr esters in Journal f. prakt. Chemie 317(6), p. 890-896 (1975); ibid. 318(3), p. 403-408 (1976) and ibid. 320(2), p. 344-350 (1978). No potential application of these compounds was provided in the description.

W. Lehnert reported in Tetrahedron 30, p. 301-305 (1974) a method for the preparation of simple phenylethenylidene-diphosphonate and-carboxyphosphonate esters, without any information on their potential application.

The U.S. Pat. No. 4,696,920 (1987) of Symphar S.A. reports the preparation of tetraethyl and tetrabutyl 2-(3,5-ditertiobutyl-4-hydroxy)benzyl-1,3-propylidenediphosphonate and their possible use in the treatment of cardiovascular diseases induced by or associated with the dysfunction of the slow calcium channels.

The UK patent 2 043 072 (1979) of Symphar S.A. discloses the synthesis of unsubstituted phenyl- and phenoxyalkylidene-1,1-diphosphonic acids and Me and Et esters and their application as antiatherosclerotic agents.

The present invention relates to compounds of formula (I):

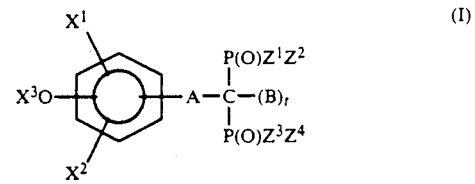

where:

$Z^1$, $Z^2$, $Z^3$ and $Z^4$ identical or different are

OR where R is H, a straight, branched or cyclic alkyl group comprising from 1 to 8 carbon atoms, OM where M is an alkali or alkaline earth metal ion or an ammonium group $NR_4$ where R has the same meaning as defined above, $NR_2$ where R has the same meaning as defined above, $Z^1$, $Z^2$ and $Z^3$, $Z^4$ may form an alkylidenedioxy ring comprising 2 to 8 carbon atoms.

$X^1$, $X^2$ identical or different, are H, a halogen atom, a straight, branched or cyclic alkyl or alkoxy group from 1 to 8 carbon atoms, $X^3$ is H, an alkyl group $R^1$ from 1 to 4 carbon atoms, an acyl group $C(O)R^1$, a carbamyl group $C(O)NHR^1$ were $R^1$ is described as above; $X^3O$ and one of the two other substituents $X^1$ or $X^2$ may form an alkylidenedioxy ring comprising from 1 to 4 carbon atoms, A is $-CH=CH-CH_2-$, $-(CH_2)_n-$, $-S-$, $SO_2$, $-S(CH_2)_n-$, $-SO_2(CH_2)_n-$, where n is an integer from 1 to 7, $-(CH=CH)_k-(CH_2)_d-CH=$ where k is zero or 1 and d is an integer from zero to 4, B is H, an alkyl group from 1 to 4 carbon atoms, t is zero or 1, with the proviso that t is zero only when A is $(CH=CH)_k-(CH_2)_d-CH=$ where k and d are as described above. The compounds of formula (I) include the phenol substituted alkylidenediphosphonates (Ia) and the phenol substituted alkenylidenediphosphonates (Ib)

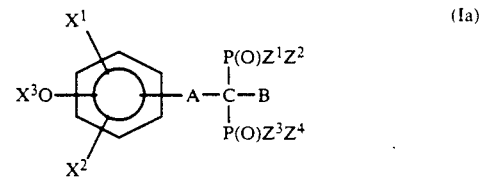

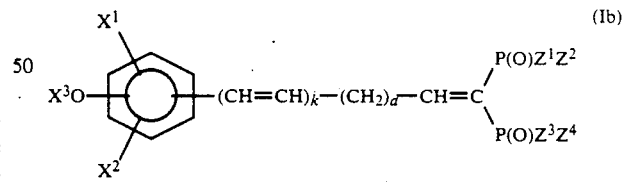

where $X^1$, $X^2$, $X^3$, A, B, k, d, $Z^1$, $Z^2$, $Z^3$, $Z^4$ are as described above.

Compounds of structure (Ia) include, for example, those in which:

$X^1$, $X^2$ identical or different are alkyl groups from 1 to 8 carbon atoms, $X^3$ is hydrogen, A is $CH=CH-CH_2$, $(CH_2)_n$, S, $SO_2$, $S-(CH_2)_n$, $SO_2-(CH_2)_n$, where n is 1-7, B is hydrogen or a $C_1-C_4$ alkyl group.

$Z^1$, $Z^2$, $Z^3$, $Z^4$ identical or different are OH, alkoxy groups of 1 to 8 carbon atoms or one or both of the pairs $Z^1$, $Z^2$ and $Z^3$, $Z^4$ are an alkylidenedioxy group of 2 to 8 carbon atoms.

Compounds of structure (Ib) include, for example, those in which $X^1$, $X^2$ identical or different are alkyl groups from 1 to 8 carbon atoms, $X^3$ is hydrogen, k is zero or 1 and d is zero to 4, $Z^1$, $Z^2$, $Z^3$, $Z^4$ identical or different are OH, alkoxy groups of 1 to 8 carbon atoms or one or both of the pairs $Z^1$, $Z^2$ and $Z^3$, $Z^4$ are an alkylidenedioxy group of 2 to 8 carbon atoms.

PROCESS FOR PREPARING COMPOUNDS OF FORMULA (I)

The present invention also relates to a process for preparing gem-diphosphonates of formula (Ia) and (Ib).

The experimental procedure for preparing (Ia) consists in reacting the diphosphonate compound III with a base such as sodium hydride, sodium metal, sodium alkoxide, n-butyl lithium or lithium diisopropylamide. The starting product II is then reacted with the anion of compound III thus formed in situ to give the substituted diphosphonate (Ia). The reaction takes place in solvents such as hexane, heptane, benzene, toluene, tetrahydrofuran, dioxane, dimethoxyethane, methyl tertiobutyl ether or N, N-dimethylformamide. The solvents can be utilized pure or as a mixture, depending on the solvent polarity desired. The temperature range of the reaction is between $-78°$ C. and the boiling point of the solvent or solvent mixture. The reaction time varies between several hours and several days. In the case where A is a sulfur atom, the appropriate starting compound II is the bis (substituted phenol) disulfide and the preferred base is n-butyl lithium.

The procedure for preparing (Ib) consists in condensing the appropriate aldehyde IV with the diphosphonate compound V using titanium tetrachloride and a tertiary amine such as methyl morpholine or pyridine as catalysts. The reaction is carried out in an ether solvent such as tetrahydrofuran, dioxane or dimethoxyethane. The polarity of the reaction medium can be conveniently modified by adding a non-polar solvent such as tetrachloromethane. The temperature of the reaction varies between $-15°$ C. and $40°$ C., preferably between $0°$ C. and $30°$ C.

The obtained alkenylidene-diphosphonates (Ib) can be hydrogenated to the corresponding alkylidene-diphosphonates (Ia) where B=H. In the particular case where structure (Ib) contains two double bonds, i.e. when k=1, the reduction conditions can be made to form either of the following two compounds (Ia): the partially saturated compound where A=(CH=CH-)$_k$—(CH$_2$)$_d$—CH$_2$, B=H, or the completely saturated compound where A=(CH$_2$—CH$_2$)$_k$—(CH$_2$)$_d$—CH$_2$, B=H.

The partially saturated compound (Ia) where A=(CH=CH)$_k$—(CH$_2$)$_d$—CH$_2$, B=H, can be made predominantly when (Ib), where k=1, is reduced with a complex hydride reagent such as sodium borohydride or lithium borohydride in a polar solvent which can be methanol, ethanol at a temperature between $-15°$ and room temperature.

The completely saturated compound (Ia) where A=(CH$_2$CH$_2$)$_k$—(CH$_2$)$_d$—CH$_2$, B=H, can be obtained from (Ib), where k=1, by reduction with an excess of complex hydride reagent such as sodium borohydride or lithium borohydride in methanol or ethanol as solvent at a temperature between room and reflux temperature. Another convenient reduction method is the catalytic hydrogenation using palladium or platinum adsorbed on active charcoal as catalyst. Suitable solvents include methanol, ethanol, dimethoxyethane, dioxane, tetrahydrofuran and acetic acid. The reduction is performed at room temperature and at a pressure between 1 and 4 atm.

Compounds (I) obtained through one of the procedures described in page 8 can be derivatized into other products with different ester groups. One such method involves the hydrolysis of the tetraethyl ester compounds (I), $Z^1$-$Z^4$=OEt, with hydrochloric acid or bromotrimethylsilane/water to yield the corresponding diphosphonic acids (I), $Z^1$-$Z^4$=OH. The latter compounds are alkylated by using trialkyl orthoformates to form the corresponding tetraalkyl esters. An alternative method consists in reacting the tetraethyl ester derivative with bromotrimethylsilane/phosphorus pentachloride to form the diphosphonyl tetrachloride. The esterification of this intermediate with various alcohols or diols yields new derivatives (I) where the pairs of substituents $Z^1$, $Z^2$ and $Z^3$, $Z^4$ may be individual alkoxy groups or may form alkylidenedioxy groups.

The above described synthetic procedures are described immediately hereafter.

SYNTHETIC PROCEDURE

General preparation of (Ia)

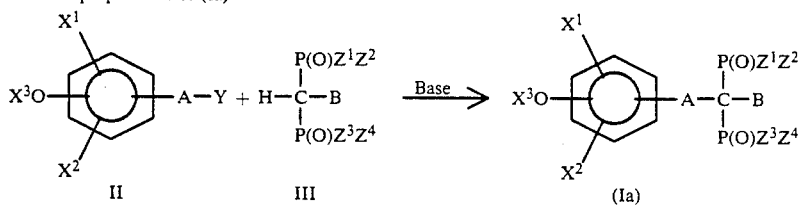

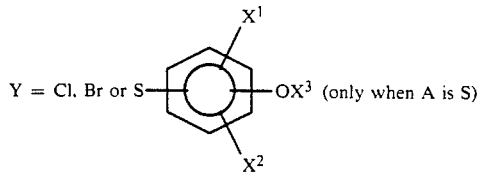

Y = Cl, Br or S—[ring]—OX$^3$ (only when A is S)

-continued
SYNTHETIC PROCEDURE
Preparation of (Ib) and (Ia) when B = H and A = (CH=CH)$_k$—(CH$_2$)$_d$—CH$_2$ and (CH$_2$CH$_2$)$_k$—(CH$_2$)$_d$—CH$_2$ where k = zero or 1 and d = zero to 4
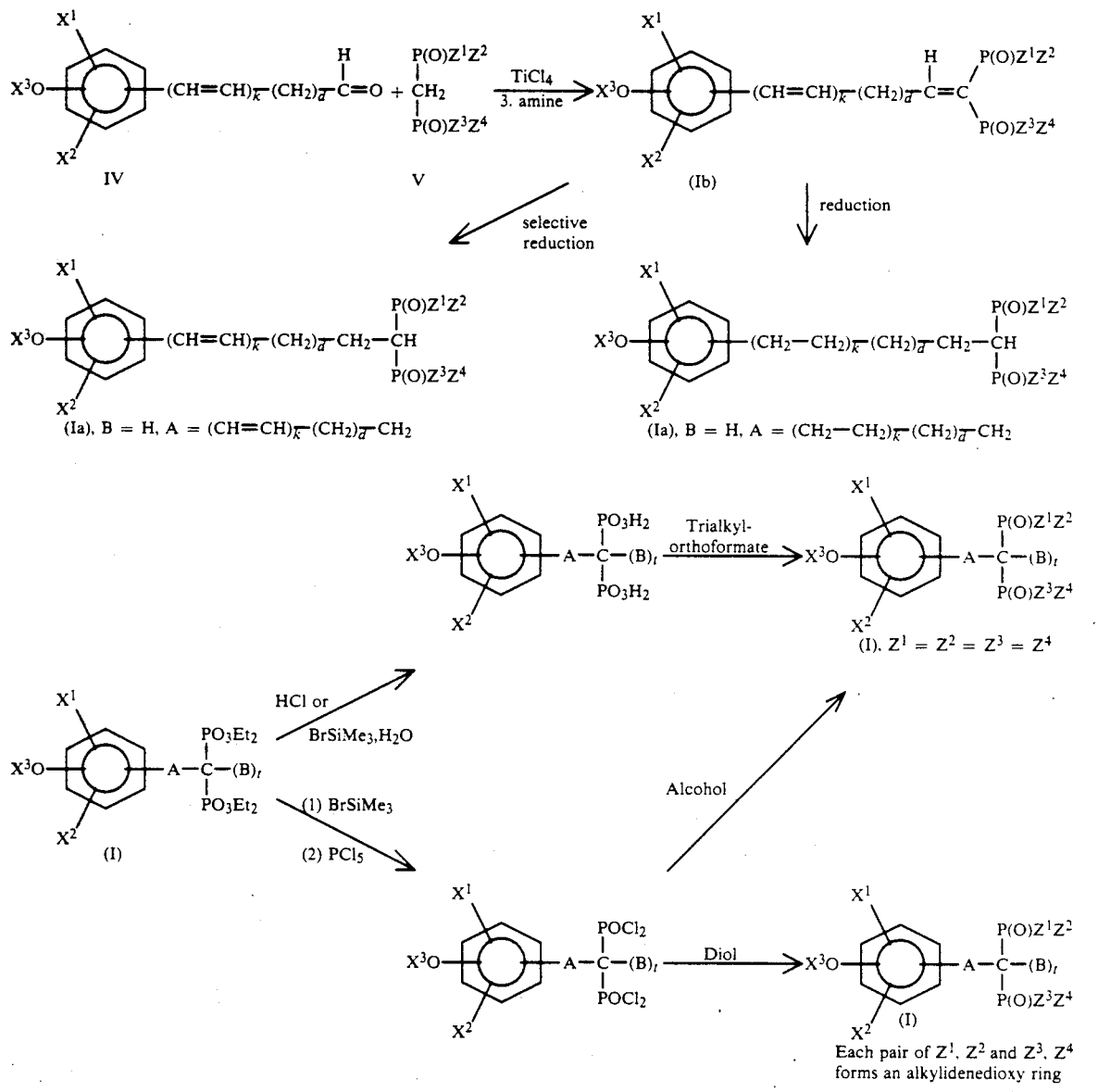
When A is S—(CH$_2$)$_n$ or O—(CH$_2$)$_n$, (Ia) can also be prepared by reacting bromoalkylidenediphosphonate VIII with respectively the thiohydroquinone VI or hydroquinone derivative VII in presence of a base.
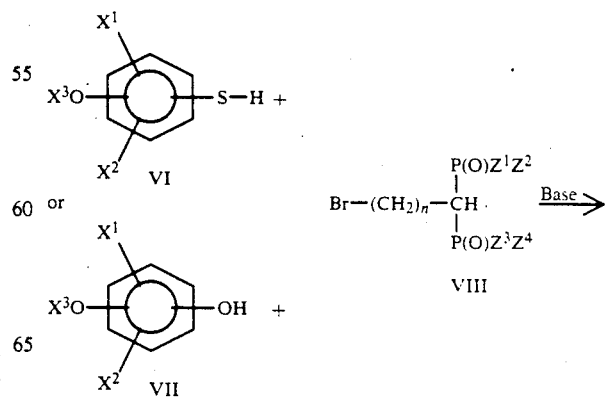

-continued

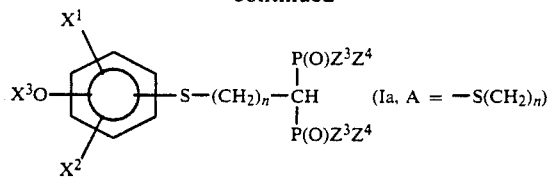
(Ia, A = —S(CH₂)ₙ)

or

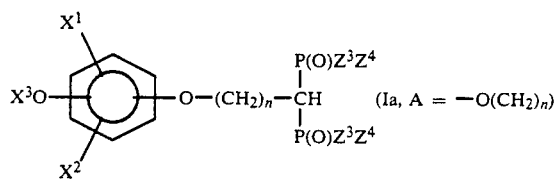
(Ia, A = —O(CH₂)ₙ)

When A is S—(CH₃)ₙ where n≧3, one additional method for preparing (Ia) involves reacting VI with an alkenylidene-diphosphonate IX in presence of a radical initiating agent such as benzoyl peroxide or hydrogen peroxide.

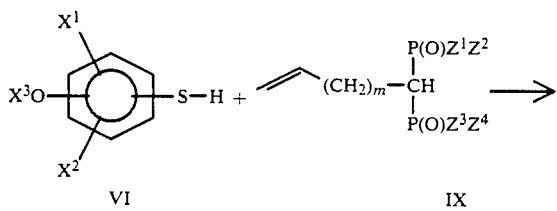

VI          IX

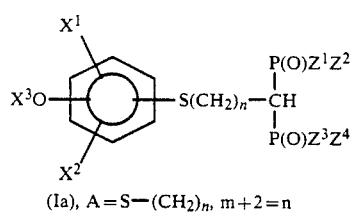

(Ia), A=S—(CH₂)ₙ, m+2=n

The sulfide group is converted to the higher oxidation states, namely the sulfone groups, by using an oxidative agent which may be a peracid such as m-chloroperbenzoic acid or a peroxide salt such as potassium permanganate or potassium hydrogen persulfate.

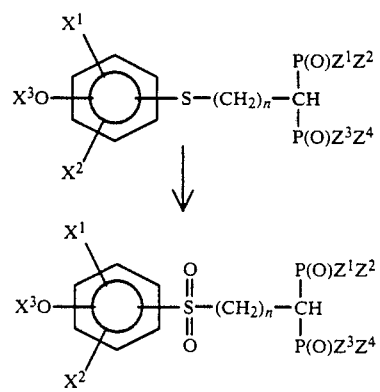

Compounds (I) where $X^3$ is different from H can be prepared by using the corresponding starting compound II where $X^3 \neq H$. One alternative method involves derivatizing the phenolic —OH group in compounds (I) by standard synthetic procedures: alkylation, by reacting the phenoxide anion with alkylating reagents such as alkyl halide or dialkyl sulfate, esterification by using acylating reagents such as acid anhydrides or acyl halides to form the corresponding esters or by using isocyanates to form the corresponding carbamates.

The starting compounds V which are not commercially available are prepared by one of the two following methods.

Arbuzov reaction between an alkyl phosphite and a halogenomethylphosphonate

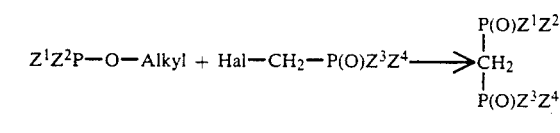

V

Transesterification of the methylenediphosphonate ethyl ester

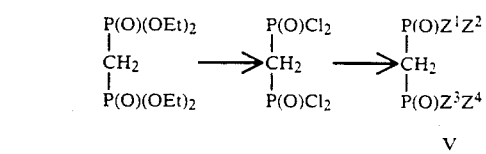

V

These two methods provide new starting compounds V where the substituents $Z^1$, $Z^2$, $Z^3$, $Z^4$ may be individual alkoxy groups or where the pairs of substituents $Z^1$, $Z^2$ and/or $Z^3$, $Z^4$ may form alkylidenedioxy rings. The structures of compounds of formula (I) are determined by elemental analysis, infrared (IR), mass (MS) and nuclear magnetic resonance (NMR) spectroscopies. The purity of the compounds is verified by thin layer chromatography (Silicagel, CH₂Cl₂/MeOH or CHCl₃/MeOH eluent mixtures), gas liquid chromatography (Methyl silicone column) or high performance liquid chromatography (Octadecylsilane C₁₈ reversed phase column).

The abbreviations used in this patent application are as follows:

In Tables 1 and 2, n- is normal, i- is iso-, sec is secondary-, t is tertiary. In the NMR spectra, s is singlet, d is doublet, t is triplet, m is multiplet. The temperatures are measured in degree Celsius and the melting points are uncorrected. The boiling points refer to values obtained by short path distillation carried out in a ball tube type distillation apparatus (Kugelrohr).

The present invention will be further described by the Examples 1 to 23 which are typical of the synthetic procedures used.

EXAMPLE 1

Tetrabutyl 2-(3,5-ditertiarybuty-4-hydroxyphenyl)-ethylidene-1,1-diphosphonate

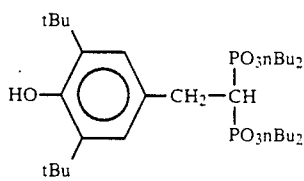

A solution of 3,5-ditertiobutyl-4-hydroxybenzyl bromide (2.48 g, 8.3 mmol) in 30 ml dioxane was added to a solution of 12.5 mmol of sodium tetrabutyl methylenediphosphonate prepared by reacting an equimolar amount of NaH and tetrabutyl methylenediphosphonate in 30 ml tetrahydrofuran. The reaction mixture was refluxed for 16 h then was partitioned between $H_2O$ and $CHCl_3$. The dried organic phase ($MgSO_4$) was evaporated and the residue was purified by column chromatography ($SiO_2$, $CHCl_3$ then 95/5 $CHCl_3$/MeOH) to afford 2.9 g (4.6 mmol, 56%) of tetrabutyl 2-(3,5-diteriarybutyl-4-hydroxyphenyl)-ethylidene-1,1-diphosphonate.

IR (film):
2980 $cm^{-1}$: aliphatic C—H
1440: t-$C_4H_9$
1240: P=O
1020–970: P—O—C
NMR ($CDCl_3$):
$\delta =$
7.05 (s, 2H): aromatic H
5.08 (s, 1H) OH
4.1–3.95 (m, 8H): P—O—$CH_2$—$C_3H_7$
3.18 (t×d, J=7 and 16 Hz, 2H): Ph—$CH_2$—
2.66 (t×t, J=7 and 24 Hz, 1H): Ph—$CH_2$—CH
1.60 (sextet, J=7 Hz, 8H): P—O—$CH_2CH_2$—$C_2H_5$
1.44 (s, 18H): t-$C_4$-$H_9$
1.38 (multiplet, J=7 Hz, 8H): P—O—$C_2H_4$—$CH_2$—$CH_3$
0.90 (2×t, J=7 Hz, 12H): P—O—$C_3H_6$—$CH_3$

EXAMPLE 2

Compound 5

Tetraethyl 3,5-ditertiarybutyl-4-hydroxyphenylthio-methylenediphosphonate

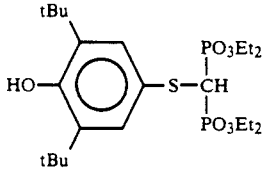

To a solution of tetraethyl methylenediphosphonate (2.43 g, 8.43 mmol) in 15 ml dry tetrahydrofuran were added 5.3 ml (8.43 mmol) of 1.6 M n-butyllithium in hexane at −78° under nitrogen. To the above solution were then added 15 ml of a tetrahydrofuran solution of 4.0 g (8.43 mmol) of bis(3,5-ditertiary-butyl-4-hydroxyphenyl)disulfide, prepared according to T. Fujisawa et al., Synthesis 1972, p. 624-625. The mixture was maintained at −78° C. for 1 h and then stirred at 25° C. for 3 days. Hydrolysis was performed with 20 ml saturated $NH_4Cl$ solution and the mixture was extracted with 3×40 ml diethyl ether. The organic phase was dried over $MgSO_4$, evaporated and the residue was purified by column chromatography ($SiO_2$, 95/5 $CH_2Cl_2$/MeOH). It was obtained 2.2 g (4.2 mmol) of a yellow oil which slowly crystallized; yield=49%.
mp=78°-80° C.
Elemental analysis $C_{23}H_{42}O_7P_2S$;
% calc. C, 52.66; H, 8.07; P, 11.88; S, 6.11;
% found C, 52.13; H, 7.77; P, 11.65; S, 6.62;
IR (film):
3600+3450 $cm^{-1}$: OH
1430: t-$C_4H_9$
1250: P=O
1040: P—O—C
NMR ($CDCl_3$):
$\delta =$
7.5 (s, 2H): aromatic H
5.4 (s, 1H): OH
4.35-4.2 (m, 8H): P—O—$CH_2CH_3$
3.55 (t, J=21 Hz, 1H): —CH—$PO_3Et_2$
1.45 (s, 18H): t-$C_4H_9$
1.35 (t, J—7 Hz, 12H): P—O—$CH_2$—$CH_3$
MS: 524 ($M^+$)

EXAMPLE 3

Compound 4

Tetraethyl 2-(3,5-ditertiarybutyl-4-hydroxyphenyl)-ethylidene-1,1-diphosphonate

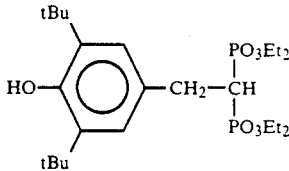

Tetraethyl methylenediphosphonate (21.2 g, 73.5 mmol) was added at room temperature to a 80% dispersion of sodium hydride in mineral oil (2.2 g, 73.5 mmol) suspended in 70 ml dry benzene. To this solution of sodium tetraethyl methylenediphosphonate was then added a 30 ml toluene solution of 20 g (66.8 mmol) of 3,5-ditertiarybutyl-4-hydroxybenzylbromide prepared according to H. Gross, H. Seibt and I. Keitel, Journal für prakt. Chemie 317 (6), p. 890–896 (1975). The resulting mixture was refluxed for hours. The cooled toluene phase was extracted with $H_2O$, dried over $MgSO_4$ and evaporated to dryness. The residue was purified by column chromatography ($SiO_2$, pure $CHCl_3$ followed by a 95/5 $CHCl_3$/MeOH solution) to give 21.3 g (63% yield) of tetraethyl 2-(3,5-ditertiarybutyl-4-hydroxyphenyl)-ethylidene-1,1-diphosphonate.
mp=62°-63° C.
Elemental analysis $C_{24}H_{44}O_7P_2$;
% calc. C, 56.90; H, 8.76; P, 12.23;
% found C, 56.76; H, 8.53; P, 12.15.
IR (KBr):
3400 $cm^{-1}$: O—H
2850: aliphatic C—H
1440: t-butyl
1240: P=O
1040: P—O—C
NMR ($CDCl_3$):
$\delta =$
7.1 (s, 2H): aromatic H
5.1 (s, 1H): OH
4.15-4.05 (m, 8H): P—O—$CH_2CH_3$
3.18 (t×d, J=6 and 17 Hz, 2H): Ph—$CH_2$
2.65 (t×t, J=6 and 24 Hz, 1H): Ph—$CH_2$—H
1.45 (s, 18H): t$C_4$—$H_9$
1.26 (two overlapping t, J=7 Hz, 12H): P—O—$CH_3$

EXAMPLE 4

Compound 13

Tetraethyl 2-(3,4-methylenedioxy-6-chlorophenyl)-ethylidene-1,1-diphosphonate

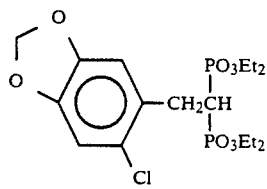

To a solution of sodium tetraethyl methylenediphosphonate (22 mmol) in 15 ml dry dimethoxyethane were added 4.1 g (20 mmol) of 6-chloropiperonyl chloride. After 16 h at reflux the reaction mixture was partitioned between $Et_2O$ (3×20 ml) and $H_2O$ (20 ml) and the organic phase was dried over $MgSO_4$. Short path distillation Kugelrohr) gave 3.1 g (8.5 mmol, 43%) of the title compound.

bp=200° C./0.05 mmHg
IR (film)
2950 cm$^{-1}$: aliphatic C—H
1240: P=O
1030: P—O—C+OCH$_2$O
Elemental analysis: $C_{17}H_{27}ClO_8P_2$;
% calc. C, 44.70; H, 5.96; P, 13.56; Cl, 7.56;
% found C, 44.51; H, 6.21; P, 13.41; Cl, 7.65.
NMR (CDCl$_3$):
δ=
6.76 (s, 1H): aromatic H
6.70 (s, 1H): aromatic H
5.84 (s, 2H): O—C$\underline{H_2}$—O
4.10–3.96 (m, 8H): P—O—C$\underline{H_2}$CH$_3$
3.10–3.20 (m, 2H): Ph—C$\underline{H_2}$
2.80 (t×t, J=7 and 24 Hz, 1H): Ph—CH$_2$C$\underline{H}$
1.12 (two overlapping t, J=7 Hz, 12H): P—O—CH$_2$—C$\underline{H_3}$

EXAMPLE 5

Compound 30

Tetraethyl 2-(3-tertiobutyl-4-hydroxy-5-methylphenyl)ethenylidene-1,1-diphosphonate

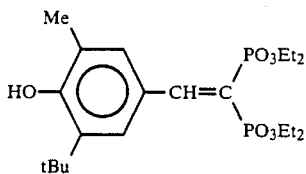

Under nitrogen, 300 ml of dry tetrahydrofuran were placed in a 500 ml reactor and were cooled to 0°. Titanium tetrachloride (27.5 g, 145 mmol) was added dropwise followed by 10 g (52 mmol) of 3-tertiobutyl-4-hydroxy-5-methylbenzaldehyde synthesized according to G.A. Nikiforov et al., Izv. Akad. Nauk SSSR, Otd. Khim. Nauk 1962, p. 1836-8; Chem. Abst. 58, 7856f (1963). Tetraethyl methylenediphosphonate (21 g, 72 mmol) was added followed by pyridine (22.9 g, 290 mmol). The mixture was stirred for 3 h at room temperature and concentrated under vacuum. The residue was partitioned between $Et_2O$ and $H_2O$. The ether phase was washed with $NaHCO_3$ solution to pH 7, dried and evaporated to dryness. An amount of 18.5 g (40 mmol, 77% yield) was obtained of the title compound, pure by GLC.

IR (film):
3400 cm$^{-1}$: OH
2950: aliphatic C—H
1240: P=O
1060: P—O—C
NMR (CDCl$_3$):
δ=
8.2 (d×d, J=30 and 50 Hz, 1H): Ph—C$\underline{H}$=CP$_2$
7.7–7.6 (m, 2H): aromatic H
4.25–4.05 (m, 8H): P—O—C$\underline{H_2}$CH$_3$
2.25 (s, 3H): C$\underline{H_3}$
1.4 (s, 9H): t-C$\underline{_4H_9}$
1.35 and 1.2 (2×t, 12H): P—O—CH$_2$—C$\underline{H_3}$

EXAMPLE 6

Compound 3

Tetraethyl 2-(3,5-ditertiarybutyl-4-hydroxyphenyl)-ethenylidene-1,1-diphosphonate

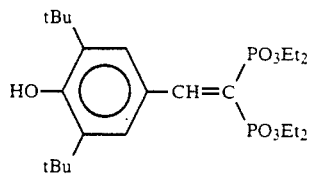

An amount of 700 ml dry tetrahydrofuran was placed in a 1 l reactor under nitrogen atmosphere. Titanium tetrachloride (96.5 g, 0.51 mol) was added to the THF solution cooled to 0°, followed by 40.0 g (0.17 mol) 3,5-ditertiobutyl-4-hydroxybenzaldehyde. Tetraethyl methylenediphosphonate (69.1 g, 0.24 mol) was added dropwise, followed by methylmorpholine (97.6 g, 0.97 mol) and the resulting mixture was stirred at room temperature for 4 h. The reaction mixture was then partitioned between $H_2O$ and diethyl ether. The ether phase was washed until neutral pH, dried and evaporated. The residue was recrystallized in acetone and the mother liquor purified by column chromatography (SiO$_2$, pure CHCl$_3$ followed by 95/5 CHCl$_3$/MeOH). The combined fractions gave 53 g (0.11 mol, 62% yield) of tetraethyl 2-(3,5-ditertiobutyl-4-hydroxyphenyl)-ethenylidene-1,1-diphosphonate.

mp=120°–121° C.
Elemental analysis $C_{24}H_{42}O_7P_2$;
% calc. C, 57.14; H, 8.39; P, 12.28;
% found C, 56.89; H, 8.23; P, 12.05.
IR (KBr):
3200 cm$^{-1}$: OH
2850: aliphatic C—H
1570: C=C
1440: t-butyl
1240: P=O
1060: P—O—C
NMR (CDCl$_3$):
δ=
8.25 (d×d, J=30 and 48 Hz, 1H): Ph—C$\underline{H}$=C—P$_2$
7.7 (m, 2H): aromatic H
5.65 (s, 1H): OH 4.2–4.0 (2×m, 8H): P—O—CH$_2$—CH$_3$
1.5 and 1.45 (2×s, 18H): t-C$_4$H$_9$
1.4 and 1.2 (2×t, 12H): P—O—CH$_2$CH$_3$

EXAMPLE 7

Compound 38

Tetraethyl 2-(3,4-methylenedioxyphenyl)-ethenylidene-1,1-diphosphonate

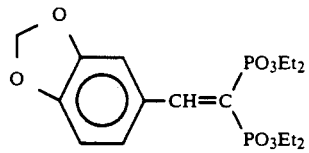

Under nitrogen, TiCl$_4$ (11 ml, 100 mmol) was added dropwise to a 200 ml solution of dry THF cooled to 0° C. Sequentially were added piperonal (7.5 g, 50 mmol) dissolved in 30 ml THF, tetraethyl methylenediphosphonate (14.4 g, 50 mmol) and N-methylmorpholine (20.2 g, 200 mmol). The mixture was stirred at room temperature for 90 min, H$_2$O (50 ml) was added and the resulting mixture was extracted by Et$_2$O (3×100 ml). The residue of the organic phase was purified by column chromatography (SiO$_2$, 95/5 CHCl$_3$/MeOH) to give 13.7 g (32.6 mmol, 66%) of the title compound.

IR (film): 2980, 1560 (C=C), 1250 (P=O), 1030 (P—O—C)

Elemental analysis: C$_{17}$H$_{26}$O$_8$P$_2$;
% calc. C, 48.58; H, 6.24; P, 14.74;
% found C, 48.20; H, 6.01; P, 14.21.
NMR (CDCl$_3$):
δ=
8.26–8.04 (d×d, J=48 and 30 Hz, 1H): Ph—CH=C
7.52 (S, 1H): aromatic H
7.28 (d, 1H): aromatic H
6.80 (d, 1H): aromatic H
5.98 (S, 2H): O—CH$_2$—O
4.15 and 4.05 (two m, 8H): P—O—CH$_2$CH$_3$
1.30 and 1.16 (two t, 12H): P—O—CH$_2$CH$_3$

EXAMPLE 8

Compound I

Tetraethyl 2-(3-tertiobutyl-4-hydroxy-5-methylphenyl)-ethylidene-1,1-diphosphonate

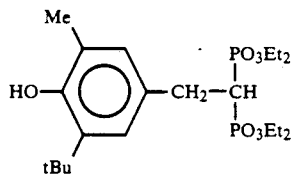

An amount of 11.4 g (24.6 mmol) of tetraethyl 2-(3-tertiobutyl-4-hydroxy-5-methylphenyl)-ethenylidene-1,1-diphosphonate was added to a solution of 4.65 g (123 mmol) NaBH$_4$ in EtOH and the mixture was refluxed for 90 min. The ethanol solution was evaporated and the residue was partitioned between 2.5 N HCl and Et$_2$O. Evaporation of the dried organic phase gave an oil which was purified by short-path distillation. 9.9 g (87% yield) of tetraethyl 2-(3-tertiobutyl-4-hydroxy-5-methylphenyl)-ethylidene-1,1-diphosphonate were obtained.

bp=190° C. (0.05 mmHg)
Elemental analysis C$_{21}$H$_{38}$O$_7$P$_2$;
% calc. C, 54.30; H, 8.25; P, 13.34;
% found C, 54.04, H, 8.15; P, 12.94.
IR (film):
3400 cm$^{-1}$: OH
2850: aliphatic C—H
1240: P=O
1060: P—O—C
NMR (CDCl$_3$):
δ=
7.0–6.9 (m, 2H): aromatic H
4.2–4.05 (m, 8H): P—O—CH$_2$—CH$_3$
3.14 (d×t, J=6 and 18 Hz, 2H): Ph—CH$_2$
2.6 (t×t, J=6 and 24 Hz, 1H): Ph—CH$_2$—CH
2.2 (s, 3H): CH$_3$
1.4 (s, 9H): t-C$_4$H$_9$
1.25 (2×t, 12H): P—O—CH$_2$—CH$_3$

EXAMPLE 9

Compound 4

Tetraethyl 2-(3,5-ditertiarybutyl-4-hydroxyphenyl)-ethylidene-1,1-diphosphonate

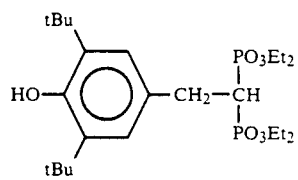

A 80 ml ethanol solution of tetraethyl 2-(3,5-ditertiobutyl-4-hydroxyphenyl)-ethenylidene-1,1-diphosphonate (25.3 g, 50 mmol) (compound 33) was added under nitrogen to a suspension of lithium borohydride (3.3 g, 150 mmol) in 250 ml ethanol and the mixture was refluxed for 1 h. The solvent was evaporated and the residue was taken up in diethyl ether. The ether phase was washed with a 10% HCl solution, H$_2$O until pH 6 and then dried over MgSO$_4$. Evaporation of the ether solution gave 24 g (47 mmol, 95% yield) of tetraethyl 2-(3,5-ditertiobutyl-4-hydroxyphenyl)-ethylidene-1,1-diphosphonate.

The reduction of compound 33 can also be carried out by catalytic hydrogenation.

A mixture of compound 33 (1 g, 2 mmol) and 20 mg of 10% Palladium on active charcoal (10% Pd/C) in 50 ml acetic acid was hydrogenated at room temperature and 1.5 atm pressure for 16 h. Filtration of the catalyst and evaporation of the solvent gave 1.0 g (2 mmol, 100%) of the title compound.

Platinum on active charcoal (10% Pt/C) can also be used with equally good results. A mixture of compound 33 (1 g, 2 mmol) and 20 mg 10% Pt/C in 50 ml CH$_3$COOH was hydrogenated at room temperature and 1.2 atm for 16 h and gave after work up 1 g of compound 4 (2 mmol, 100%).

The compound prepared by these reduction procedures has physical and spectroscopic data identical to those of the product described in Example 3.

EXAMPLE 10

Compound 8

2-(3,5-ditertiarybutyl-4-hydroxyphenyl)-ethylidene-1,1-diphosphonic acid

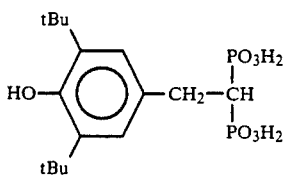

Under anhydrous conditions, trimethylbromosilane (5 ml, 38.6 mmol) was added dropwise to 10 ml of a carbon, tetrachloride solution of tetraethyl 2-(3,5-ditertiarybutyl-4-hydroxyphenyl)ethylidene-1,1-diphosphonate 1.95 g, 3.86 mmol). The mixture was stirred at room temperature for 30 h. The excess of $BrSiMe_3$ was removed by distillation and the residue was treated with 20 ml $H_2O$ for 2 h. Evaporation of the aqueous solution gave 1.43 g (3.6 mol, 94%) of the diphosphonic acid.

mp=177°-178° C.
IR (KBr):
3600 cm$^{-1}$: OH
3000-2500: P—O—H
1430: t-$C_4H_9$
1200: P=O

Compound 8 can also be obtained by hydrolysis with hydrochloric acid.

A mixture of compound 4 (2.5 g, 50 mmol) in 10 ml 37% HCl was heated to 115° for 16 h. The evaporation d of HCl provided 1.9g (4.8 mmol, 96%) of 2-(3,5-ditertiarybutyl-4-hydroxyphenyl)-ethylidene-1,1-diphosphonic acid.

EXAMPLE 11

Compound 10

Tetramethyl 2-(3 5-ditertiarybutyl-4-hydroxyphenyl)-ethylidene-1,1-diphosphonate

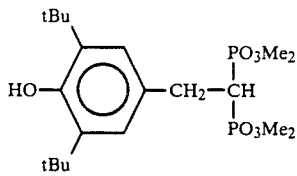

A mixture of 3.5 g (8.9 mmol) 2-(3,5-ditertiarybutyl-4-hydroxypheny)-ethylidene-1,1-diphosphonic acid and 10 g (94 mmol) trimethylorthoformate was refluxed for one hour. The methyl formate and methanol formed were distilled off. Fresh trimethyl orthoformate (10 g, 94 mmol) was added and the mixture was refluxed for one hour. Removal of excess reagent and short path distillation (200° C. 0.05 mmHg) gave 2.5 g (65%) of tetramethyl 2-(3,5-ditertiarybutyl-4-hydroxyphenyl)-ethylidene-1,1-diphosphonate.

mp=77°-78° C.
IR(KBr):
3400 cm$^{-1}$: O—H
2850: aliphatic C—H
1430: t-butyl
1245: P=O
1185: P—O—Me
1030: P—O—C.
NMR (CDCl$_3$):
δ=
7.25 and 7.05 (m, 2H): aromatic H
5.0 (s, 1H): OH
3.7-3.65 (two d, J=11 Hz, 12H): P—O—CH$_3$
3.1 (t×d, J=6 and 17 Hz, 2H): Ph—CH$_2$
2.6 (t×t, J=6 and 24 Hz, 1H): Ph—CH$_2$—CH
1.35 (s, 18H) : t-C$_4$H$_9$

EXAMPLE 12

Compound 15

Tetraethyl 1-(3,5-ditertiarybutyl-4-methoxyphenyl)propylidene 2,2-diphosphonate

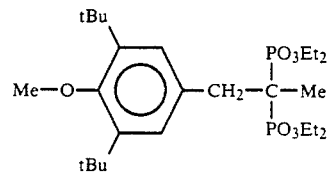

Tetraethyl 2-(3,5-ditertiarybutyl-4-hydroxyphenyl)-ethylidene-1,1-diphosphonate (500 mg, 1 mmol) was added to a suspension of 80% NaH (40 mg, 1.3 mmol) in 20 ml dry THF. Methyl iodide (1.3 ml, mmol) was added and the reaction mixture was refluxed for 16 h. After Et$_2$O/H$_2$O extraction, the organic phase was dried and evaporated. Column chromatography (SiO$_2$, 95/5 CHCl$_3$/MeOH) gave 440 mg (0.84 mmol, 84%) of the title compound.

IR:
2980 cm$^{-1}$: aliphatic C—H
1240: P=O
1030: P—O—C
MS 534 (M$^+$), 397 (100%, M—PO$_3$Et$_2$)$^-$, 233

EXAMPLE 13

Compound 41

Tetraethyl 2-(3,5-ditertiarybutyl-4-acetoxyphenyl)-ethenylidene-1,1-diphosphonate

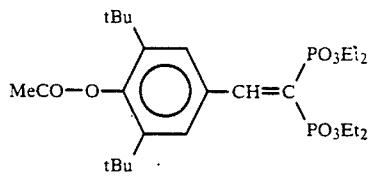

A mixture of tetraethyl 2-(3,5-ditertiarybutyl-4-hydroxyphenyl)ethenylidene-1,1-diphosphonate (3 g, 6 mmol) and a catalytic amount (50 mg) H$_2$SO$_4$ in 3 g of acetic anhydride was warmed to 80° C. for 3 h. The reaction mixture was poured on ice and extracted in Et$_2$O. The organic phase was washed with H$_2$O and dried over MgSO$_4$ and evaporated to dryness. The residue was purified by column chromatography (SiO$_2$, 95/5 CHCl$_3$/MeOH) to give 2.32 g (4.2 mmol, 71% yield) of the title compound.

IR:
2840 cm$^1$: aliphatic C—H
1760: C=O

1560: C=C
1240: P=O
1030: P—O—C

EXAMPLE 14

Compound 17

Tetraethyl 4-(3,5-ditertiarybutyl-4-hydroxyphenylthio)-butylidene-1,1-diphosphonate

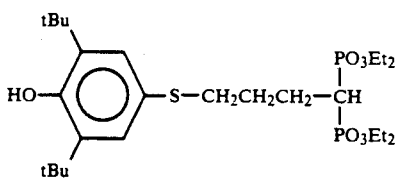

A mixture of 1.0 g (3.04 mmol) of tetraethyl 3-butenylidene-1,1-diphosphonate prepared by reaction of tetraethyl methylene diphosphonate and allyl bromide, 0.8 g (3.36 mmol) of 3,5-ditertiobutyl-4-hydroxyphenylmercaptan and 0.022 g (0.09 mmol) of dibenzoylperoxide was refluxed in benzene overnight. After evaporation of the solvent, the crude product was column chromatographied and 0.44 g (25% yield) of tetraethyl 4-(3,5-ditertiobutyl-4-hydroxyphenylthio)-butylidene-1,1-diphosphonate was isolated.

IR (film):
3400 cm$^{-1}$: O—H
2850: aliphatic C—H
1430: t-butyl
1240: P=O
1020: P—O—C
MS: 566 (M$^+$), 429 (M—PO$_3$Et$_2$)$^+$

EXAMPLE 15

Compound 19

Diethyl 1-bis(dimethylamino)phosphinyl-2-(3,5-ditertiarybutyl-4hydroxyphenyl)ethylphosphonate

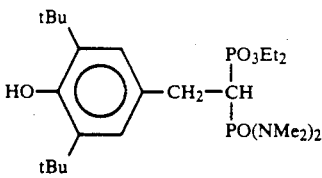

Diethyl bis(dimethylamino)phosphinyl methylphosphonate was prepared by reacting diethyl methylphosphonate and bis(dimethylamino) phosphorochloridate using lithium diisopropylamide in THF, according to P. Savignac et al, Tetrahedron Letters 26 (37), p. 4435-4438 (1985).

Diethyl bis(dimethylamino)phosphinyl methylphosphonate (1.4 g, mmol) was added at room temperature to a suspension of 80% NaH (0.15 g, 5 mmol) in 20 ml dry tetrahydrofuran. A solution of 3,5-ditertiarybutyl-4-hydroxybenzylbromide (1.5 g, 5 mmol) in 20 dioxane was added and the mixture was refluxed overnight. After evaporation of the solvents, the residue was partitioned between H$_2$O and CHCl$_3$. The residue of the organic phase was purified by column chromatography (SiO$_2$, 95/5 CHCl$_3$/MeOH) to give 490 mg (20% yield) of the title compound.

IR (film):
3400 cm$^{-1}$: OH
2860: aliphatic C—H
1440: t-C$_4$H$_9$
1240+1220: P=O
1030: P—O—C
MS: (m/e)$^+$: 504 (M$^+$); 369 (100%, M$^+$—PO(NMe$_2$)$_2$); 135 (PO(NMe$_2$)$_2$)$^+$
NMR (CDCl$_3$)
δ=
7.08 (s, 2H): aromatic H
5.08 (s, 1H): OH
4.1-3.9 (m, 4H): P—O—CH$_2$CH$_3$
3.25-3.1 (large m, 2H : Ph—CH$_2$—CH
2.9-2.7 (large m, 1H): Ph—CH$_2$—CH
2.5 and 2.55 (two d, J=9 Hz, 12H): N—CH$_3$
1.38 (s, 18H): t-C$_4$H$_9$
1.15 (two t, J=7 Hz, 6H): P—O—CH$_2$CH$_3$

EXAMPLE 16

Compound 16

Tetraethyl 3,5-ditertiarybutyl-4-hydroxyphenylsulfonylmethylenediphosphonate

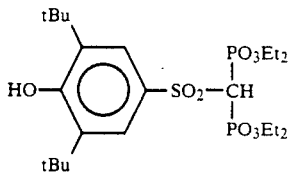

A solution of 800 mg (1.26 mmol) of 49.5% KHSO$_5$ (Potassium hydrogen persulfate, "oxone") in 0.8 ml H$_2$O was added to a solution of 400 mg of tetraethyl 3,5-ditertiarybutyl-4-hydroxyphenylthio-methylene diphosphonate (compound 5) (0.84 mmol) in 5 ml CH$_3$OH while stirring in an ice bath. The resulting slurry is The residue is partitioned between H$_2$O and CH$_2$Cl$_2$. The organic phase is washed with H$_2$O until neutral pH, concentrated and the residue is purified by column chromatography (CHCl$_3$/MeOH). An amount of 200 mg (0.36 mmol, 29%) of tetraethyl 3,5-diteriarybutyl-4-hydroxyphenylsulfonyl-methylenediphosphonate was obtained.

mp=118°-120° C.

MS: (m/e): 556 (M$^+$), 492 ((M—SO$_2$)$^+$, 100%), 355 (M—PO$_3$Et$_2$)$^+$

A mixture of compound 5 (400 mg, 0.76 mmol) and 85% m-chloroperbenzoic acid (0.5 g, 2.5 mmol) in 5 ml CH$_2$Cl$_2$ was stirred at room temperature for 16 h. The organic solution was extracted with saturated NaHSO$_3$, saturated NaHCO$_3$ and dried over MgSO$_4$. Column chromatography purification (CHCl$_3$/MeOH) gave 160 mg of compound 16 (0.28 mmol, 38%).

EXAMPLE 17

Compound 42

Dibutyl diethyl 2-(3,5-ditertiarybutyl-4-hydroxyphenyl)-ethenylidene-1,1-diphosphonate

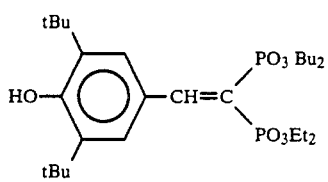

Dibutyl diethyl methylenediphosphonate was prepared in 43% yield by reacting sodium dibutyl phosphite with diethyl chloromethylphosphonate, bp=140° (0.05 mmHg), (Kugelrohr).

Dibutyl diethyl 2-(3,5-ditertiobutyl-4-hydroxyphenyl)-ethenylidene-1,1-diphosphonate was synthesized by reacting $TiCl_4$ (4.94 g, 26 mmol), 3,5-ditertiarybutyl-4-hydroxybenzaldehyde (3 g, 13 mmol), dibutyl diethyl methylenediphosphonate (4.4 g, 13 mmol) and N-methylmorpholine (5.25 g, 52 mmol) in 20 ml THF at room temperature. Column chromatography (95/5 $CHCl_3$/MeOH) afforded 2.6 g (4.6 mmol, 36%) of the title compound.

IR (film):
2980 $cm^{-1}$: aliphatic C—H
1560: C=C
1430: t-$C_4H_9$
1240: P=O
1020–970: P—O—C MS: (m/e): 560 (M+), 423 (M—$PO_3Et_2$)+, 367 (M—$PO_3Bu_2$)+, 311

EXAMPLE 18

Compound 21

Tetraethyl 1-(3,5-ditertiarybutyl-4-hydroxyphenyl)-butylidene-2,2-diphosphonate

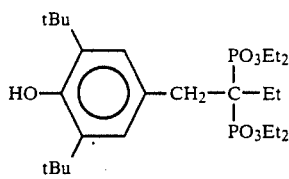

Tetraethyl propylidene-1,1-diphosphonate was prepared in 65% yield by reacting tetraethyl methylenediphosphonate with ethyl iodide in presence of NaH in tetrahydrofuran.

Tetraethyl propylidene-1,1-diphosphonate (1.5 g, 4.75 mmol) was added to a suspension of 80% NaH (0.143 g, 4.75 mmol) in dry THF (10 m) and the mixture was stirred until the NaH disappeared. 3,5-ditertiarybutyl-4-hydroxybenzylbromide (1,42 g, 4,75 mmol) in 5 ml THF was added and the mixture was refluxed for 4 h. After work up, column chromatography ($SiO_2$, 95/5 $CHCl_3$/MeOH) gave 0.9 g (1.7 mmol, 36%) of the title compound. mp=107°–110° C.

IR (film):
3400 $cm^{-1}$: OH
2850: aliphatic C—H
1440: t-butyl
1240: P=O
1040: P—O—C NMR ($CDCl_3$)
$\delta =$
7.15 (m, 2H): aromatic H
5.1 (s, 1H): OH
4.2–4.04 (m, 8H): O—$CH_2$—$CH_3$
3.2 (two d, J=12 and 16 Hz, 2H): Ph—$\underline{CH}_2$—$CP_2$
2.1–1.9 (m, 2H): —C($P_2$)—$\underline{CH}_2$—$CH_3$
1.45 (s, 18H): t$C_4H_9$
1.3–1.15 (several t, J=7 Hz, 15H): —C($P_2$)—$CH_2$—$\underline{CH}_3$ + O—$CH_2\underline{CH}_3$

EXAMPLE 19

Compound 20

Tetraethyl 7-(3,5-ditertiarybutyl-4-hydroxyphenylthio)-heptylidene-1,1-diphosphonate

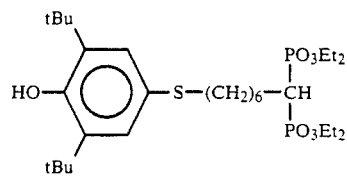

Tetraethyl 7-bromoheptylidene-1,1-diphosphonate was prepared by reaction of sodium tetraethyl methylenediphosphonate with 1,6-dibromohexane.

A 20 ml tetrahydrofuran solution containing 4.2 mmol of the sodium salt of 3,5-diteriarybutyl-4-hydroxyphenyl mercaptan was added to 20 ml of a tetrahydrofuran solution containing tetraethyl 7-bromoheptylidene-1,1-diphosphonate (1,89 g, 4.2 mmol). The reaction mixture was stirred at room temperature overnight. After hydrolysis and extraction into $Et_2O$, the crude compound was purified by column chromatography ($SiO_2$, 95/5 $CHCl_3$/MeOH) to yield 1.6 g (2.63 mmol, 62%) of the title compound.

IR (film):
3400 $cm^{-1}$: OH
2940: aliphatic C—H
1430: t-$C_4H_9$
1250: P=O
1030+980: P—O—C MS: (m/e): 608 (M+), 371, 288 (100%), 152

EXAMPLE 20

Compound 24

2-(3,5-ditertiarybutyl-4-hydroxyphenyl)ethylidene-1,1-bis (2-oxo-1,3,2-dioxaphosphorinan)

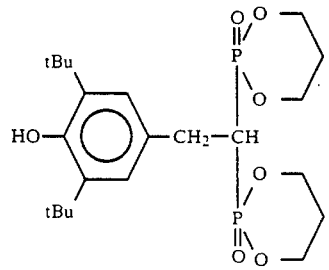

Treatment of tetraethyl 2-(3,5-ditertiobutyl-4-hydroxyphenyl)ethylidene-1,1-diphosphonate with BrSiMe₃ gave the corresponding tetrakis (trimethylsilyl) diphosphonate. This latter compound was reacted with PCl in CCl₄ according to the reaction conditions described by T. Morita et al., Chemistry Letters p. 435-438 (1980) to afford 2-(3,5-ditertiarybutyl-4-hydroxyphenyl)ethylidene-1,1diphosphonyl tetrachloride.

To a solution of Et₃N (7.86 g, 78 mmol) in 80 ml dioxane held at 55° were added simultaneously the above described diphosphonyl tetrachloride (9.0 g, 19 mmol) in 40 ml dioxane and 1,3-propanediol (2.90 g, 38 mmol) in 40 ml dioxane. The reaction mixture was refluxed for 3 h after the end of the addition. The precipitate of Et₃N.HCl was removed by filtration and the filtrate was purified by column chromatography (SiO₂, CHCl₃/MeOH 95/5). An amount of 1.35 g (2.9 mmol, 15% yield) of the title compound was obtained.

mp = 175°–176° C.
IR (KBr) = 3400, 1430, 1260 (P=O), 1040 (P—O—C)
MS (m/e)⁺ = 474 (M⁺), 353 (100%, M—PO₃(C₃H₆)₂)⁺
NMR (CDCl₃)
δ =
7.25 and 7.1 (m, 2H): aromatic H
5.1 (s, 1H):OH
4.45, 4.3 and 4.1 (3m, 8H): P—O—(CH₂)—
3.26 (d×t, J=6 and 17 Hz, 2H):Ph—C$\underline{H}_2$—
2.80 (t×t, J=7 and 23 Hz, 1H): Ph—CH₂—C$\underline{H}$
2.1 and 1.9 (2m, 4H): P—O—CH₂—C$\underline{H}_2$—CH₂
1.4 (s, 18H): t-C₄H₉

EXAMPLE 21

Compound 43

Tetraethyl 4-(3,5-ditertiarybutyl-4-hydroxyphenyl)-1,3-butadienylidene-1,1-diphosphonate

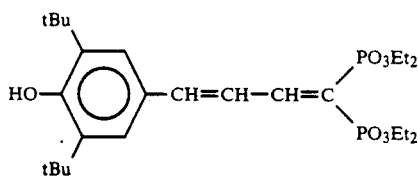

Titanium tetrachloride (3.14g, 0.017 mol) was dropped, under nitrogen, to 40 ml of anhydrous THF cooled in an ice bath. It was successively added 2.15 g (0.008 mol) of 3,5-ditertiarybutyl-4-hydroxy-cinnamaldehyde, 2.39g (0.008 mol) of tetraethyl methylenediphosphonate and 3.25 g (0.033 mol) of methylmorpholine. The resulting mixture was kept in the ice bath for a further 1 hour then allowed to return to room temperature overnight. 50 ml of water was added and the resulting mixture was extracted with 3×50 ml of ethyl ether. The combined organic phase was washed with 3×50 ml of brine, dried over magnesium sulfate and evaporated. The residue was purified by column chromatography (SiO₂, 95/5 CHCl₃/MeOH) to give 3.6 g (0.0068 mol, 82%) of the crude title compound. The latter was recrystallized from acetone yielding 2.1 g (0.0040 mol, 48%) of pure product. Melting point was 141°-143° C. giving a deep red solution.

IR(KBr):
3360 cm⁻¹: OH
1600, 1550 and 1530: C=C
1420 and 1430: tC₄H₉
1200: P=O
1020: P—O—C
MS: m/e: 530 (M⁺), 515 (M—Me), 393 (M—PO₃Et₂)
NMR (CDCl₃)
δ =
8.05–7.7 (several m, 2H): C=C$\underline{H}$—C$\underline{H}$=C
7.4 (s, 2H): aromatic H
7.04 (d, J=15 Hz, 1H): Ph—C$\underline{H}$=C
5.6 (s, 1H): OH
4.2 (m, 8H): P—O—C$\underline{H}_2$CH₃
1.45 (s, 18H): t-C₂H₉
1.35 (t, J=7Hz, 12H): P—O—CH₂C$\underline{H}_3$

EXAMPLE 22

Compound 45

Diethyl 2-(3,5-ditertiarybutyl-4-hydroxyphenyl) 1-(2-oxo-1,3,2-dioxaphosphorin-2-yl)ethenyl-1-phosphonate

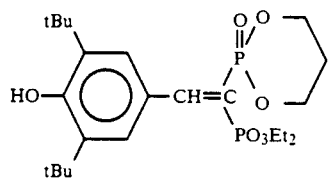

Diethyl (2-oxo-1,3,2-dioxaphosphorin-2-yl)methylphosphonate was prepared by the Arbuzov reaction of triethyl phosphite and 2-chloromethyl-2-oxo-1,3,2-dioxaphosphorinan. (IR: 1260 and 1030 cm⁻¹).

The general reaction conditions described in example 6 were employed using diethyl (2-oxo-1,3,2-dioxaphosphorin-2-yl) methylphosphonate as the phosphonate reagent. After work up, purification by column chromatography gave the title compound as an oil in 63% yield.

IR (Film): 3450cm⁻¹, 1570 (C=C), 1420, 1260, 1030 (P—O—C)
MS: 488 (M⁺), 367 (M—PO₃Et₂)⁺, 351 (M—PO₃(CH₂)₃)⁺, 57 (t-Bu)
NMR (CDCl₃)=
8.2 (d×d, J=30 and 48 Hz, 1H): Ph—C$\underline{H}$=CP₂
7.75 (m, 2H): aromatic H
5.65 (m, 1H): OH
4.3–4.0 (several m, 8H): P—O—C$\underline{H}_2$—CH₃ and P—O—C$\underline{H}_2$—CH₂—CH₂
2.1–1.6 (several m, 2H): P—O—CH₂—C$\underline{H}_2$—CH₂
1.4 (s, 18H): t-C₄H₉
1.4 (t, J=7Hz): P—O—CH₂—C$\underline{H}_3$

EXAMPLE 23

Compound 28

Tetraethyl 4-(3,5-ditertiarybutyl-4-hydroxyphenyl)-butylidene-1,1-diphosphonate

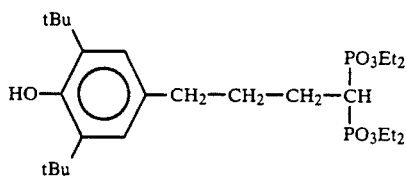

0.5 g (0.94 mmol) of tetreethyl 4-(3,5-ditertiarybutyl-4-hydroxyphenyl)-1,3-butadienylidene-1,1-diphosphonate (compound 43), 0.23 g of 10% palladium on active charcoal in 25 ml of glacial acetic acid were submitted to 3 atm. hydrogen gas in a Parr hydrogenation apparatus until no more absorption was observed. The catalyst was filtered. The filtrate was diluted with an equal volume of water and extracted with chloroform. The chloroform phase was washed successively with 10% NaOH, water and dried over $MgSO_4$. Evaporation of the solvent gave 0.4 g of the title compound (98% purity by GC).

IR (film)=
3400 $cm^{-1}$: O—H
2940: aliphatic C—H
1440: t-butyl
1250: P=O
1020: P—O—C NMR ($CDCl_3$):
$\delta$ =
6.96 (s, 2H) : aromatic H
5.03 (s, 1H): OH
4.24–4.10 (m, 8H): P—O—$CH_2$—$CH_3$
2.52 (t, J=7 Hz, 2H): Ph—$\underline{CH}_2$—
2.28 (t×t, J=6 and 24 Hz, 1$\overline{H}$): Ph—$CH_2$—$CH_2$—$CH_2$—$CHP_2$
2.04–1.78 (2×m, 4H): Ph—$CH_2$—$\underline{CH}_2$—$\underline{CH}_2$—$CHP_2$
1.40 (s, 18H): $tC_4\underline{H}_9$
1.28 (two overlapping t, J=7 Hz, 12H): P—O—$CH_2$—$CH_3$ MS: $\overline{5}$34 (M+)

This compound was chromatophically and spectroscopically identical to the material isolated from the reaction of 3-(3,5-ditertiarybutyl-4-hydroxyphenyl)-propyl bromide (mp=52°–54° C.) with the sodium salt of tetraethyl methylenediphosphonate in benzene.

TABLE 1

Phenol substituted gem-diphosphonates (Ia)

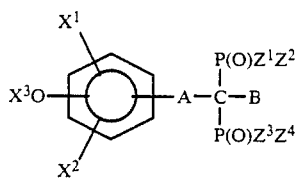

(Ia)

| Cpd | $X^1$ | $X^2$ | $X^3$ | A | B | $Z^1$ | $Z^2$ | $Z^3$ | $Z^4$ | mp or bp (mm Hg). °C. | Formula[a] |
|---|---|---|---|---|---|---|---|---|---|---|---|
| 1 | 3-Me | 5-t-Bu | 4-H | $CH_2$ | H | OEt | OEt | OEt | OEt | 190(0.05) | $C_{21}H_{38}O_7P_2$ |
| 2 | 3-i-Pr | 5-i-Pr | 4-H | $CH_2$ | H | OEt | OEt | OEt | OEt | 195(0.05) | $C_{22}H_{40}O_7P_2$ |
| 3 | 3-sec-Bu | 5-sec-Bu | 4-H | $CH_2$ | H | OEt | OEt | OEt | OEt | 200(0.05) | $C_{24}H_{44}O_7P_2$ |
| 4 | 3-t-Bu | 5-t-Bu | 4-H | $CH_2$ | H | OEt | OEt | OEt | OEt | 62–63 | $C_{24}H_{44}O_7P_2$ |
| 5 | 3-t-Bu | 5-t-Bu | 4-H | S | H | OEt | OEt | OEt | OEt | 78–80 | $C_{23}H_{42}O_7P_2S$ |
| 6 | 3-t-Bu | 5-t-Bu | 4-H | $CH_2$ | H | Oi—Pr | Oi—Pr | Oi—Pr | Oi—Pr | 104–105 | $C_{28}H_{52}O_7P_2$ |
| 7 | 3-t-Bu | 5-t-Bu | 4-H | $CH_2$ | H | On—Bu | On—Bu | On—Bu | On—Bu | b | $C_{32}H_{60}O_7P_2$ |
| 8 | 3-t-Bu | 5-t-Bu | 4-H | $CH_2$ | H | OH | OH | OH | OH | 177–178 | c |
| 9 | 3-t-Bu | 5-t-Bu | 4-H | S | H | OH | OH | OH | OH | 183–185 | c |
| 10 | 3-t-Bu | 5-t-Bu | 4-H | $CH_2$ | H | OMe | OMe | OMe | OMe | 77–78 | $C_{20}H_{36}O_7P_2$ |
| 11 | 3-OMe | 5-OMe | 4-H | $CH_2$ | H | OEt | OEt | OEt | OEt | b | d |
| 12 | 3-OMe | 5-OMe | 4-Me | $CH_2$ | H | OEt | OEt | OEt | OEt | 205(0.05) | $C_{19}H_{34}O_9P_2$ |
| 13 | 6-Cl | 3,4-$OCH_2$— | | $CH_2$ | H | OEt | OEt | OEt | OEt | 200(0.05) | $C_{17}H_{27}ClO_8P_2$ |
| 14 | 3-t-Bu | 5-t-Bu | H | $(CH_2)_2$ | H | OEt | OEt | OEt | OEt | b | $C_{25}H_{46}O_7P_2$ |
| 15 | 3-t-Bu | 5-t-Bu | Me | $CH_2$ | Me | OEt | OEt | OEt | OEt | b | $C_{26}H_{48}O_7P_2$ |
| 16 | 3-t-Bu | 5-t-Bu | 4-H | $SO_2$ | H | OEt | OEt | OEt | OEt | 118–120 | $C_{23}H_{42}O_9P_2S$ |
| 17 | 3-t-Bu | 5-t-Bu | 4-H | $S(CH_2)_3$ | H | OEt | OEt | OEt | OEt | b | d |
| 18 | 3-t-Bu | 5-t-Bu | 4-H | $CH_2$ | H | OEt | OEt | On—Bu | On—Bu | b | $C_{28}H_{52}O_7P_2$ |
| 19 | 3-t-Bu | 5-t-Bu | 4-H | $CH_2$ | H | OEt | OEt | $NMe_2$ | $NMe_2$ | b | $C_{24}H_{46}N_2O_5P_2$ |
| 20 | 3-t-Bu | 5-t-Bu | 4-H | $S(CH_2)_6$ | H | OEt | OEt | OEt | OEt | b | $C_{29}H_{54}O_7P_2S$ |
| 21 | 3-t-Bu | 5-t-Bu | 4-H | $CH_2$ | Et | OEt | OEt | OEt | OEt | 107–110 | $C_{26}H_{48}O_7P_2$ |
| 22 | 3-t-Bu | 5-t-Bu | 4-H | S | H | Oi—Pr | Oi—Pr | Oi—Pr | Oi—Pr | 106–108 | $C_{17}H_{50}O_7P_2S$ |
| 23 | 3-t-Bu | 5-t-Bu | 4-H | $CH_2$ | H | On—Pr | On—Pr | On—Pr | On—Pr | 73–74 | $C_{28}H_{52}O_7P_2$ |
| 24 | 3-t-Bu | 5-t-Bu | 4-H | $CH_2$ | H | O—$(CH_2)_3$—O | | O—$(CH_2)_3$O | | 173–174 | $C_{22}H_{36}O_7P_2$ |
| 25 | 3-t-Bu | 5-t-Bu | 4-H | $CH_2$ | H | OEt | OEt | Oi—Pr | Oi—Pr | 59–60 | $C_{26}H_{48}O_7P_2$ |
| 26 | 3-sec-Bu | 5-sec-Bu | 4-H | $CH_2$ | H | Oi—Pr | Oi—Pr | Oi—Pr | Oi—Pr | b | $C_{28}H_{52}O_7P_2$ |
| 27 | 3-t-Bu | 5-t-Bu | 4-H | $CH_2$ | H | $OCH_2$—$CMe_2$—$CH_2O$ | | $OCH_2$—$CMe_2$—$CH_2O$ | | 66–67 | $C_{26}H_{44}O_7P_2$ |
| 28 | 3-t-Bu | 5-t-Bu | 4-H | $(CH_2)_3$ | H | OEt | OEt | OEt | OEt | b | d |

TABLE 1-continued
Phenol substituted gem-diphosphonates (Ia)

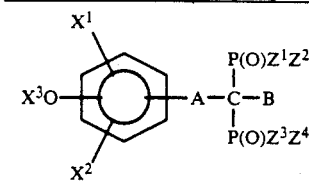

(Ia)

| Cpd | $X^1$ | $X^2$ | $X^3$ | A | B | $Z^1$ | $Z^2$ | $Z^3$ | $Z^4$ | mp or bp (mm Hg), °C. | Formula[a] |
|---|---|---|---|---|---|---|---|---|---|---|---|
| 29 | 3-t-Bu | 5-t-Bu | 4-H | CH=CH—CH$_2$ | H | OEt | OEt | OEt | OEt | b | d | a = analyzed for C, H, P; results within 0.4% of theoretical values
b = purified by column chromatography
c = characterized by NaOH titration
d = characterized by IR and MS spectroscopies

TABLE 2
Phenol substituted gem-diphosphonates (Ib)

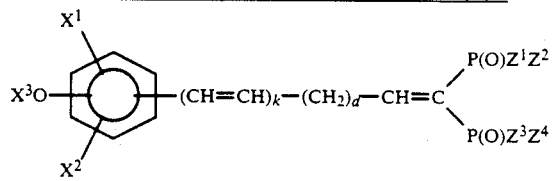

(Ib)

| Compound | $X^1$ | $X^2$ | $X^3$ | k | d | $Z^1$ | $Z^2$ | $Z^3$ | $Z^4$ | mp or bp (mm Hg), °C. | Formula[a] |
|---|---|---|---|---|---|---|---|---|---|---|---|
| 30 | 3-Me | 5-t-Bu | 4-H | 0 | 0 | OEt | OEt | OEt | OEt | b | $C_{21}H_{36}O_7P_2$ |
| 31 | 3-i-Pr | 5-i-Pr | 4-H | 0 | 0 | OEt | OEt | OEt | OEt | 97-100 | $C_{22}H_{38}O_7P_2$ |
| 32 | 3-sec-Bu | 5-sec-Bu | 4-H | 0 | 0 | OEt | OEt | OEt | OEt | 102-105 | $C_{24}H_{42}O_7P_2$ |
| 33 | 3-t-Bu | 5-t-Bu | 4-H | 0 | 0 | OEt | OEt | OEt | OEt | 120-121 | $C_{24}H_{42}O_7P_2$ |
| 34 | 3-t-Bu | 5-t-Bu | 4-H | 0 | 0 | Oi—Pr | Oi—Pr | Oi—Pr | Oi—Pr | 131-132 | $C_{28}H_{50}O_7P_2$ |
| 35 | 3-t-Bu | 5-t-Bu | 4-H | 0 | 0 | On—Bu | On—Bu | On—Bu | On—Bu | 59-61 | $C_{32}H_{58}O_7P_2$ |
| 36 | 3-t-Bu | 5-t-Bu | 4-H | 0 | 0 | OH | OH | OH | OH | 135-137 | c |
| 37 | 3-OMe | 5-OMe | 4-H | 0 | 0 | OEt | OEt | OEt | OEt | 53-55 | $C_{18}H_{30}O_9P_2$ |
| 38 | H | 3,4-OCH$_2$— | | 0 | 0 | OEt | OEt | OEt | OEt | b | $C_{17}H_{26}O_8P_2$ |
| 39 | H | 3,4-O(CH$_2$)$_2$— | | 0 | 0 | OEt | OEt | OEt | OEt | b | $C_{18}H_{28}O_8P_2$ |
| 40 | 3-t-Bu | 5-t-Bu | 4-Me | 0 | 0 | OEt | OEt | OEt | OEt | b | $C_{24}H_{44}O_7P_2$ |
| 41 | 3-t-Bu | 5-t-Bu | 4-MeCO | 0 | 0 | OEt | OEt | OEt | OEt | b | $C_{26}H_{44}O_8P_2$ |
| 42 | 3-t-Bu | 5-t-Bu | 4-H | 0 | 0 | OEt | OEt | OBu | OBu | b | $C_{28}H_{50}O_7P_2$ |
| 43 | 3-t-Bu | 5-t-Bu | 4-H | 1 | 0 | OEt | OEt | OEt | OEt | 141-143 | $C_{26}H_{44}O_7P_2$ |
| 44 | 3-t-Bu | 5-t-Bu | 4-H | 0 | 2 | OEt | OEt | OEt | OEt | b | d |
| 45 | 3-t-Bu | 5-t-Bu | 4-H | 0 | 0 | O(CH$_2$)$_3$O | | OEt | OEt | b | $C_{23}H_{48}O_7P_2$ |
| 46 | 3-t-Bu | 5-t-Bu | 2-H | 0 | 0 | OEt | OEt | OEt | OEt | 143-145 | $C_{24}H_{42}O_7P_2$ |
| 47 | 3-t-Bu | 5-t-Bu | 4-H | 0 | 0 | OMe | OMe | OMe | OMe | 95-96 | $C_{20}H_{34}O_7P_2$ |
| 48 | 3-t-Bu | 5-t-Bu | 4-H | 0 | 0 | On—Pr | On—Pr | On—Pr | On—Pr | 85-87 | $C_{28}H_{50}O_7P_2$ |
| 49 | 3-t-Bu | 5-t-Bu | 4-H | 0 | 0 | OEt | OEt | Oi—Pr | Oi—Pr | 106-107 | $C_{26}H_{46}O_7P_2$ |
| 50 | 3-sec-Bu | 5-sec-Bu | 4-H | 0 | 0 | Oi—Pr | Oi—Pr | Oi—Pr | Oi—Pr | b | $C_{28}H_{50}O_7P_2$ |
| 51 | 3-t-Bu | 5-t-Bu | 4-H | 0 | 0 | O(CH$_2$)$_3$O | | O(CH$_2$)$_3$O | | 207-213 | $C_{22}H_{34}O_7P_2$ | a = analyzed for C, H, P; results within 0.4% of theoretical values
b = purified by column chromatography
c = characterized by NaOH titration
d = characterized by IR and MS spectroscopies

PHARMACOLOGICAL ACTIVITY OF GEM-DIPHOSPHONATES OF FORMULA (I)

During routine screening the gem-diphosphonate derivatives were discovered to display a spectrum of pharmacological activities, the most marked being hypolipidemia (hypocholesterolemia and/or hypotriglyceridemia). Some of the diphosphonic acid derivatives demonstrated anti-inflammatory activity and some diphosphonate esters were hypotensive. Diuretic and positive inotropic activity were also observed.

In addition it might be expected that the gem-diphosphonates possess antioxidant and radical scavenging activities associated with the dialkyl hydroxyphenyl moieties present in their structures. Free radical scavengers are known to be efficacious in preventing the pathological changes in a number of diseases induced by oxidative stress. The gem-diphosphonates are thus potentially useful for the treatment of diseases such as:

tissue ischemia such as heart and brain ischemia,
muscular dystrophy,
chronic obstructive pulmonary disease,
viral infections,
senile caractogenesis and
vitamin E deficiencies.

A) HYPOLIPIDEMIC ACTIVITY

With the goal of finding new drugs which might be hypolipidemic, the new diphosphonates described in this patent application were administered orally to mice. This rodent species has plasma lipid levels relatively close to man (generally greater than 150 mg/dl).

For example, in mice receiving a normal diet the plasma cholesterol and triglyceride levels are in the range of 100 mg/dl, whereas for rat the comparative values are close to 50 mg/dl. Other scientists have recently investigated the use of mice and found this species to be a relevant model for testing new agents in comparison to drugs known to be efficacious in human hyperlipidemia (Effects of Fenofibrate, Gemfibrozil and Nicotinic Acid on Plasma Lipoprotein Levels in Normal and Hyperlipidemic Mice, a Proposed Model for Drug Screening. Olivier, P. et al. Atherosclerosis 70, p.107–114, 1988).

1) Methods

In every screening experiment, 30 mice of the OF1 strain weighing 25 to 35 g were divided into 5 groups of 6 animals each. Four groups received the compounds to be tested, or the reference drugs, the fifth group served as control. Compounds were dissolved in diethyl ether, the solution was added to the pelleted food and the ether was evaporated.

All compounds were tested at the final concentration of 0.1% in animal chow, equivalent to a daily intake of about 180 mg/kg. This diet was fed for 10 days, then after an overnight fasting the animals were sacrificed by decapitation under ether anesthesia. Blood samples were collected in EDTA containing tubes.

Plasma cholesterol and plasma triglycerides were measured by enzymatic methods (Ames kit No. 6376 and No. 6630). The mean cholesterol or triglyceride value of each group receiving tested compounds or reference drugs was expressed as percent of the mean value observed for the contemporary control.

2) Results

Table 3 showed that a number of diphosphonate derivatives (Compounds 3, 4, 5, 6, 7, 18, 21, 22, 23, 24, 33, 34, 37, 47 and 48) were markedly hypocholesterolemic, Compounds 33 and 34 being the most potent (−40% and −41%). Clofibrate, gemfibrozil and fenofibrate, drugs used clinically for the treatment of hyperlipidemia, were found to be less hypocholesterolemic than many of the diphosphonates tested. Fenofibrate was the most potent (−15%) of the references drugs tested. Similar hypocholesterolemic activity was measured in mice receiving the fibrate derivatives as published in the reference cited above (Olivier, P. et al.).

A significant hypotriglyceridemia was observed with Compounds 3, 5, 6, 7, 21, 22, 23, 24, 30, 31, 33, 37, 47 and 48. It should be noted that Compounds 3, 19, 24, 30, 37 and 47 decreased plasma triglycerides by more than 44%, values not reached by the reference drugs tested similarly. Gemfibrozil was the most potent hypotriglyceridemic reference drug (−35%), which is in accordance with values published in the literature.

The exact mechanism by which these diphosphonates lower plasma lipids in various in vivo models is not known. However, investigations using in vitro preparations have demonstrated that these compounds inhibit and interfere with some key enzymes involved in cholesterol synthesis and metabolism, specifically acyl-CoA: cholesterol acyltransferase (ACAT), lipases, etc., and thus indicate the possible sites of action.

B) ANTI-INFLAMMATORY ACTIVITY

1) Methods

The effect of four selected diphosphonates was investigated on the inflammatory response to kappa carrageenan in the rat paw oedema model. Eight male rats were employed per group. Oedema was induced in the right hind paw of each animal by a single injection into the plantar aponeurosis of 0.1 ml of a 1% w/v of kappa carrageenan solution dissolved in 0.9% NaCl. The test compounds (100 mg/kg) and reference drug (indomethacin 30 mg/kg) were administered by gavage 1 hour prior to induction of oedema by carrageanan injection.

The volume of the right paw was measured for each animal at 0, 1, 2.5 and 4 hours after carrageenan injection (only 4 hour values are reported).

2) Results

Table 4 showed that indomethacin prevented completely the increase in paw volume as expected. Compounds 8 and 36 showed significant inhibitory activities whereas their ethyl ester counterparts demonstrated only minimal activity.

These results indicate that the diphosphonic acids such as Compound 8 are anti-inflammatory in this animal model.

C) Oral hypotensive activity in hypertensive rats

The spontaneously hypertensive rat (SHR) is a well established animal model of human arterial hypertension. The gem-diphosphonates of formula (I) were found to induce a marked hypotension when administered to SHRs.

In screening experiments various gem-diphosphonates were dissolved in Tween-80 and administered orally to SH rats. Blood pressure was monitored hourly using a tailcuff method. Hypotension measured two hours post dose are given in Table 5.

Compounds 4, 6, 7 and 18 decreased blood pressure by 30 to 50% and are as potent as the reference drugs tested similarly and which are used for the treatment of angina pectoris and hypertension.

The gem-diphosphonates of formula (I) are thus potentially useful in the treatment of cardiovascular diseases via a smooth muscle relaxant activity. The primary indications of these compounds would be the treatment of angina pectoris, congestive heart failure and hypertension.

TABLE 3

HYPOLIPIDEMIC ACTIVITY OF DIPHOSPHONATES OF FORMULA (I) AND REFERENCE DRUGS

| Compounds (I) | Cholesterol (% control) | Triglycerides (% control) |
|---|---|---|
| 1 | −2 | −28 |
| 2 | +6 | −17 |
| 4 | −12 | −1 |
| 6 | −37 | −34 |
| 7 | −23 | −15 |
| 8 | −2 | +19 |
| 10 | −5 | −19 |
| 19 | −6 | −44 |
| 3 | −19 | −46 |
| 5 | −22 | −24 |
| 33 | −40 | −21 |
| 30 | +2 | −45 |
| 31 | +4 | −11 |
| 35 | 0 | −7 |
| 36 | −9 | −5 |
| 38 | −5 | −6 |
| 13 | −5 | −38 |
| 18 | −31 | −60 |
| 20 | +5 | −13 |
| 21 | −16 | −28 |
| 22 | −21 | −37 |
| 23 | −15 | −33 |
| 24 | −20 | −71 |

TABLE 3-continued
HYPOLIPIDEMIC ACTIVITY OF DIPHOSPHONATES OF FORMULA (I) AND REFERENCE DRUGS

| Compounds (I) | Cholesterol (% control) | Triglycerides (% control) |
|---|---|---|
| 32 | +8 | +9 |
| 34 | −41 | +11 |
| 37 | −16 | −70 |
| 39 | +4 | +17 |
| 41 | −3 | +6 |
| 42 | +12 | +1 |
| 43 | −5 | −14 |
| 46 | +1 | −12 |
| 47 | −31 | −45 |
| 48 | −21 | −36 |
| Reference Drugs | | |
| Clofibrate | +4 | −5 |
| Gemfibrozil | −7 | −35 |
| Fenofibrate | −15 | −2 |

TABLE 4
ANTI-INFLAMMATORY ACTIVITY OF DIPHOSPHONATES OF FORMULA (I) AND INDOMETHACIN
Inhibition of rat right hind paw volume increase (4 hours post oedema induction)

| Compounds (I) | % Change from control |
|---|---|
| Compound 4 | +1.5 |
| Compound 8 | −54.2 |
| Compound 33 | −5.8 |
| Compound 36 | −25.0 |
| Reference Drug | |
| Indomethacin | −92.3 |

TABLE 5
EFFECT OF GEM-DIPHOSPHONATES OF FORMULA (I) ON BLOOD PRESSURE IN HYPERTENSIVE RATS
(2 hours post dose)

| Compounds (I) | Percent decrease in blood pressure |
|---|---|
| 4 | −34 |
| 6 | −64 |
| 7 | −30 |
| 18 | −41 |
| 3 | −20 |
| Reference Drugs | |
| Diltiazem | −38 |
| Nifedipine | −47 |

MODES OF ADMINISTRATION

The gem-diphosphonates of formula (I) can thus be used for the treatment of hyperlipidemia and/or hypertension and can be administered preferably in the form of capsules, tablets and granules. For this purpose the active principle should be mixed with a pharmaceutical carrier.

As used herein, the term "pharmaceutical carrier" denotes a solid or liquid filler diluent or encapsulating substance. Some examples of the substances which can serve as pharmaceutical carriers are sugars, starches, cellulose and its derivatives, powdered tragacanth, malt, gelatin, talc, stearic acid, magnesium stearate, calcium sulfate, vegetable oils, polyols and polyethylene glycol, agar, alginic acid, pyrogen-free water, isotonic saline and phosphate buffer solutions, as well as other non-toxic compatible substances used in pharmaceutical formulations. Wetting agents and lubricants such as sodium lauryl sulfate, as well as coloring agents, flavoring agents and preservatives, can also be present.

The pharmaceutical carrier employed in conjunction with the phosphonates is used at a concentration sufficient to provide a practical size to dosage relationship. Preferably the pharmaceutical carrier comprises from about 0.1% to 99% by weight of the total composition. Capsules and tablets are prepared by conventional methods using gem-diphosphonates in their liquid or cristalline form as described in the following examples:

| Example of a Capsule Formulation | |
|---|---|
| Ingredients | mg/Capsule |
| Compound 7 | 300 |
| Gelatin | 100 |
| Polyethylene glycol 1000 | 600 |
| Potassium sorbate | 0.5 |

| Example of a Tablet Formulation | |
|---|---|
| Ingredients | mg/Tablet |
| Compound 33 | 500 |
| Hydroxypropyl-methyl cellulose | 500 |
| Magnesium stearate | 3 |

For the treatment of specific disease states, composition containing a pharmaceutically acceptable gem-diphosphonate can be administered as a solution, suspension, emulsion or by intradermal, intramuscular, intravenous or intraperitoneal injection. Rectal administration of gem-diphosphonates can be performed by incorporating the active principle into conventional jelly bases to produce suppositories.

I claim:

1. Phenol substituted gem-diphosphonate derivatives of formula (I):

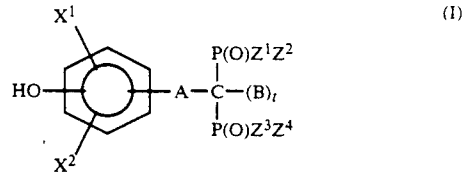

where
Z$^1$, Z$^2$, Z$^3$ and Z$^4$ identical or different are
  OR where R is H, or a straight or branched alkyl group comprising from 1 to 4 carbon atoms,
  or where Z$^1$ with Z$^2$ or Z$^3$ with Z$^4$ may form an alkyldienedixoy ring comprising from 3 to 5 carbon atoms,
X$^1$, X$^2$ identical or different, are a straight or branched alkyl group from 1 to 4 carbon atoms.
A is S, $(CH_2)_n$, or $(CH=CH)_k$—CH= where n is an integer from 1 to 3, and k is zero is 1,
B is H, or an alkyl group from 1 to 2 carbon atoms,
t is zero or 1, with the proviso that t is zero only when A is $(CH=CH)_k$—CH= where k is as described above.

2. Phenol substituted alkylidene diphosphonates of formula (Ia) according to claim 34

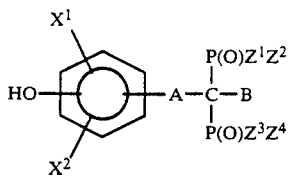

were $X^1$, $X^2$, B, $Z^1$, $Z^2$, $Z^3$, $Z^4$ are as described in claim 1 and A is S or $(CH_2)_n$ where n is an integer from 1 to 3.

3. Phenol substituted alkenylinene diphosphonates of formula (Ib) according to claim 1

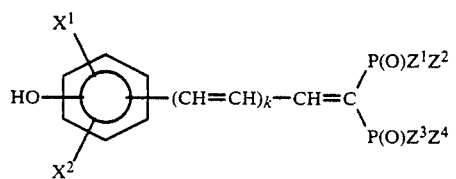

where $X^1$, $X^2$, $Z^1$, $Z^2$, $Z^3$, $Z^4$ are as described in claim 34 and k is zero or 1.

4. Tetraethyl 2-(3,5-di-secondarybutyl-4-hydroxyphenyl)-ethylidene-1,1-diphosphonate according to claim 1.

5. Tetraisopropyl (2-(3,5-ditertiarybutyl-4-hydroxyphenyl)-ethylidene-1,1-diphosphonate according to claim 1.

6. Tetraethyl 2-(3,5-ditertiarybutyl-4-hydroxyphenyl)-ethylidene-1,1-diphosphonate according to claim 1.

7. Tetraethyl 2-(3,5-ditertiarybutyl-4-hydroxyphenyl)-ethylidene-1,1-diphosphonate according to claim 1.

8. Tetraethyl 3,5-ditertiarybutyl-4-hydroxyphenylthio-methylene diphosphonate according to claim 1.

9. 2-(3,5-ditertiarybutyl-4-hydroxyphenyl)-ethylidene-1,1-bis (2-oxo-1,3,2-dioxaphosphorinan) according to claim 1.

10. 2-(3,5-ditertiarybutyl-4-hydroxyphenyl)-ethylidene-1,1-diphosphonic acid according to claim 1.

11. Tetraethyl 2-(3-tertiarybutyl-4-hydroxy-5-metylphenyl)-ethylidene-1,1-diphosphonate according to claim 1.

12. Tetraethyl 2-(3,5-ditertiarybutyl-4-hydroxyphenyl)-ethylidene-1,1-diphosphonate according to claim 1.

13. Tetraisopropyl 2-(3,5-ditertiarybutyl-4-hydroxyphenyl)-ethylidene-1,1-diphosphonate according to claim 1.

14. Tetramethyl 2-(3,5-ditertiarybutyl-4-hydroxyphenyl)-ethylidene-1,-diphosphonate according to claim 1.

15. 2-(3,5-ditertiarybutyl-4-hydroxyphenyl)-ethylidene-1,1-diphosphonic acid according to claim 1.

16. A pharmaceutical composition comprising a therapeutically effective amount of at least one diphosphonate compound of formula (I) according to claim 1 in combination with a pharmaceutically acceptable carrier.

* * * * *

UNITED STATES PATENT AND TRADEMARK OFFICE
CERTIFICATE OF CORRECTION

PATENT NO. : 5,043,330

DATED : August 27, 1991

INVENTOR(S) : Lan NGUYEN et al.

It is certified that error appears in the above—identified patent and that said Letters Patent is hereby corrected as shown below:

Column 12, line 21, change "Compound 3" to --Compound 33--.

Column 30, line 61 (claim 1, line 13 of text), change "zero is 1," to --zero or 1,--.

Column 30, line 67 (claim 2, line 2), change "34" to --1--.

Column 31, line 25, (claim 3, line 3 of text) change "34" to --1--.

Column 32, line 1 (claim 6, line 1), change "Tetraethyl" to --Tetrabutyl--.

Column 32, line 15 (claim 11, line 2), change "ethylidene" to --ethenylidene--.

Column 32, line 18 (claim 12, line 2), change "ethylidene" to --ethenylidene--.

Column 32, line 21 (claim 13, line 2), change "ethylidene" to --ethenylidene--.

Column 32, line 24 (claim 14, line 2), change "ethylidene" to --ethenylidene--.

Column 32, lines 26-27 (claim 15, lines 1-2), change "ethylidene" to --ethenylidene--.

UNITED STATES PATENT AND TRADEMARK OFFICE
CERTIFICATE OF CORRECTION

PATENT NO. : 5,043,330
DATED : August 27, 1991
INVENTOR(S) : Lan NGUYEN et al.

It is certified that error appears in the above—identified patent and that said Letters Patent is hereby corrected as shown below:

17. Tetra-n-propyl 2-(3,5-di-t-butyl-4-hydroxyphenyl)-ethylidene-1,1-diphosphonate according to claim 1.

18. Tetra-n-butyl 2-(3,5-di-t-butyl-4-hydroxyphenyl)-ethenylidene-1,1-diphosphonate according to claim 1.

19. Tetra-n-propyl 2-(3,5-di-t-butyl-4-hydroxyphenyl)-ethenylidene-1,1-diphosphonate according to claim 1.

20. Tetra-isopropyl 3,5-di-t-butyl-4-hydroxyphenylthio-methylene-diphosphonate according to claim 1.

21. A pharmaceutical composition according to claim 16, wherein said compound is tetraethyl 2-(3,5-di-t-butyl-4-hydroxyphenyl)-ethenylidene-1,1-diphosphonate.

Signed and Sealed this

Eighth Day of June, 1993

*Attest:*

MICHAEL K. KIRK

*Attesting Officer*      *Acting Commissioner of Patents and Trademarks*